United States Patent

Ament

[11] Patent Number: 5,179,926
[45] Date of Patent: Jan. 19, 1993

[54] ALCOHOL DISCRIMINATOR AND FUEL CONTROL FOR AN INTERNAL COMBUSTION ENGINE FUELED WITH ALCOHOL-GASOLINE FUEL MIXTURES

[75] Inventor: Frank Ament, Troy, Mich.

[73] Assignee: General Motors Corporation, Detroit, Mich.

[21] Appl. No.: 836,579

[22] Filed: Feb. 18, 1992

[51] Int. Cl.$^5$ .................. F02D 41/04; G01N 33/22
[52] U.S. Cl. ................. 123/494; 73/61.43; 123/1 A
[58] Field of Search ............ 123/1 A, 494, 575; 73/61.43, 61.44, 61.49

[56] References Cited

U.S. PATENT DOCUMENTS

| | | | |
|---|---|---|---|
| 4,706,630 | 11/1987 | Wineland et al. | 123/478 |
| 4,915,084 | 4/1990 | Gonze | 123/575 |
| 4,945,863 | 8/1990 | Schmitz et al. | 123/1 A |
| 4,955,345 | 9/1990 | Brown et al. | 123/381 |
| 4,971,015 | 11/1990 | Gonze | 123/494 |
| 4,989,570 | 2/1991 | Kuribara et al. | 123/494 |
| 4,993,391 | 2/1991 | Kuribara et al. | 123/482 |
| 5,003,956 | 4/1991 | Iwamoto et al. | 123/494 |
| 5,060,619 | 10/1991 | Sakurai et al. | 123/494 |

FOREIGN PATENT DOCUMENTS

0407653A1 1/1991 European Pat. Off. .
3843177A1 7/1990 Fed. Rep. of Germany .
3921707A1 1/1991 Fed. Rep. of Germany .

OTHER PUBLICATIONS

Intelligent Alcohol Fuel Sensor, by G. Schmitz, R. Bartz and U. Hilger, SAE Paper No. 900231, 1990

Primary Examiner—Tony M. Argenbright
Attorney, Agent, or Firm—Jimmy L. Funke

[57] ABSTRACT

An apparatus for discriminating between different types of alcohol contained in alcohol-gasoline fuel mixtures, such as methanol or ethanol, and a fueling system for controlling the quantity of alcohol-gasoline fuel mixture delivered to an internal combustion engine in accordance with type of alcohol determined to be present in the fuel mixture are described. The resistivity of the fuel mixture delivered to the engine is measured using a fuel resistance sensor. Based upon the measured resistivity, the type of alcohol contained in the fuel mixture is determined and indicated. The fuel system then adjusts the quantity of the fuel mixture delivered to the engine based upon the indicated type of alcohol and the sensed alcohol concentration in the fuel mixture.

13 Claims, 6 Drawing Sheets

ALCOHOL DISCRIMINATOR AND FUEL CONTROL FOR AN INTERNAL COMBUSTION ENGINE FUELED WITH ALCOHOL-GASOLINE FUEL MIXTURES

BACKGROUND OF THE INVENTION

This invention is related to the fueling of internal combustion engines with alcohol-gasoline mixtures, and more particularly, to an apparatus for discriminating between different types of alcohol, such as ethanol or methanol, contained in an alcohol-gasoline fuel mixture and a system for controlling the quantity of such a fuel delivered to an engine based upon the type of alcohol determined to be present in the fuel mixture.

To conserve oil reserves and reduce air pollution, alcohols such as ethanol and methanol are being proposed as possible alternatives to gasoline for fueling internal combustion engines. Although it is possible to operate an engine on a pure alcohol fuel, gasoline is generally blended with a particular alcohol to increase the vapor pressure of the fuel mixture to improve engine cold starting and warm-up operation.

It is well known that engines running on blended alcohol-gasoline fuels must be operated at stoichiometric air/fuel ratios depending upon on the relative proportions of the particular alcohol and gasoline in the fuel mixtures for optimal combustion. For warmed-up engine operation, this is generally accomplished by sensing the composition of the fuel mixture to determine the proper stoichiometric air/fuel ratio, and then regulating the delivery of fuel to the engine using conventional closed-loop computer control to achieve operation at the determined stoichiometric air/fuel ratio (see for example U.S. Pat. No. 4,915,084 issued to Gonze on Apr. 10, 1990).

Due to the low volatility of ethanol and methanol, the fraction of gasoline in an alcohol-gasoline mixture provides most of the combustible vapor when the engine is started, and first operated at low ambient temperatures. Consequently, engines operated on fuel mixtures having high alcohol concentrations are usually difficult to start at low temperatures, and vehicles employing such engines typically exhibit poor driveability during the engine warm-up period. The conventional approach to solving these problems has been to appropriately increase the amount of the fuel delivered to an engine during these operating periods, in accordance with the relative proportion of the particular alcohol to gasoline in the fuel mixture, to assure that a sufficient amount of gasoline vapor is present for combustion.

The problem with this approach is that conventional engine control computers are calibrated or programmed for operation with either variable ethanol-gasoline fuel mixtures or variable methanol-gasoline fuel mixtures. Hence, the type of alcohol to be used in the blended fuel mixture must be known apriori for proper fuel regulation during cold starting and engine warm-up. Once an engine control system is calibrated for a particular type of alcohol-gasoline mixture, engine cold starting and warm-up performance will generally be degraded if the engine is then operated with a fuel blend containing a different type of alcohol. This occurs because alcohol such as ethanol and methanol have different properties, and conventional fuel composition sensors calibrated for use with one type of alcohol will not indicate the correct fraction of gasoline in the fuel mixture, when another type alcohol is used in the fuel mixture to operate the engine. As a result, the fuel mixture delivered to an engine, when the closed-loop fuel control is not operable (during cold starting and warm-up), will generally be either too rich or too lean, and the engine cold starting and warm-up performance will be degraded.

Consequently, there exists a need for an apparatus capable of discriminating between alcohols such as ethanol or methanol contained in an alcohol-gasoline fuel mixture, and for a fuel control system capable of adjusting the quantity of fuel delivered to an engine based upon the type of alcohol determined to be present in the fuel mixture so the engine can be operated with different types of alcohol-gasoline fuel mixtures without degrading engine cold starting and warm-up performance.

SUMMARY OF THE INVENTION

Accordingly, it is the general object of the present invention to provide an apparatus for distinguishing between different types of alcohols such as ethanol and methanol contained in alcohol-gasoline fuel mixtures.

A further objective is to provide a system for controlling the quantity of an alcohol-gasoline fuel mixture delivered to an engine based upon type of alcohol determined to be present in the fuel mixture so that the engine can be operated with different types of alcohol-gasoline fuels without degrading engine cold starting and warm-up operation.

These and other objectives are achieved by providing a discriminator apparatus, which is capable of distinguishing between different types of alcohols in alcohol-gasoline fuel mixtures. In general, the discriminator apparatus comprises a sensor for measuring the electrical resistivity of an alcohol-gasoline fuel mixture and for developing a signal indicative of the fuel mixture resistivity; means responsive to the signal developed by the sensor for determining the type of alcohol contained in the fuel mixture; and means for providing an output signal indicative of the type of alcohol determined to be present in the fuel mixture.

More specifically, the value of the signal indicative of the fuel mixture resistivity is compared with a derived threshold resistance value. If the signal value is found to be greater than the threshold resistance value, the alcohol contained in the fuel mixture is indicated to be ethanol. If the signal value is found to be less than the value of the threshold resistive value, the alcohol contained in the fuel mixture is indicated to be methanol. The threshold resistance value may be a fixed constant, or it may be determined a function of the measured dielectric constant and/or temperature of the fuel mixture.

A system is provided for controlling engine fueling based upon the type of alcohol determined to be present in the alcohol-gasoline fuel mixture so that the engine can be operated with fuels containing different types of alcohol without degrading starting or warm-up performance. In general, the fuel control system comprises sensor means for determining the type and concentration of alcohol contained in the alcohol-gasoline fuel mixture; and means for controlling the quantity of fuel delivered to the engine based upon identified type and concentration of alcohol in the fuel mixture. Consequently, the fuel control system automatically adapts engine operation to different types of alcohol-gasoline fuel mixtures.

More specifically, resistive and capacitive sensors are employed to measure the resistivity and dielectric constant of the fuel mixture delivered to the engine. The type of alcohol contained in the fuel mixture is determined in accordance with the fuel mixture resistivity, while the alcohol concentration is determined in accordance with the determined type of alcohol and the fuel mixture dielectric constant.

These and other aspects and advantages of the invention may be best understood by reference to the following detailed description of the preferred embodiments when considered in conjunction with the accompanying drawings.

DESCRIPTION OF THE PREFERRED EMBODIMENTS

In the description that follows, similar parts or structures used in the figures will be designated with like numerals, and where such parts or structures have been previously discussed with respect to an earlier figure, the description will not be repeated.

Figure 1:
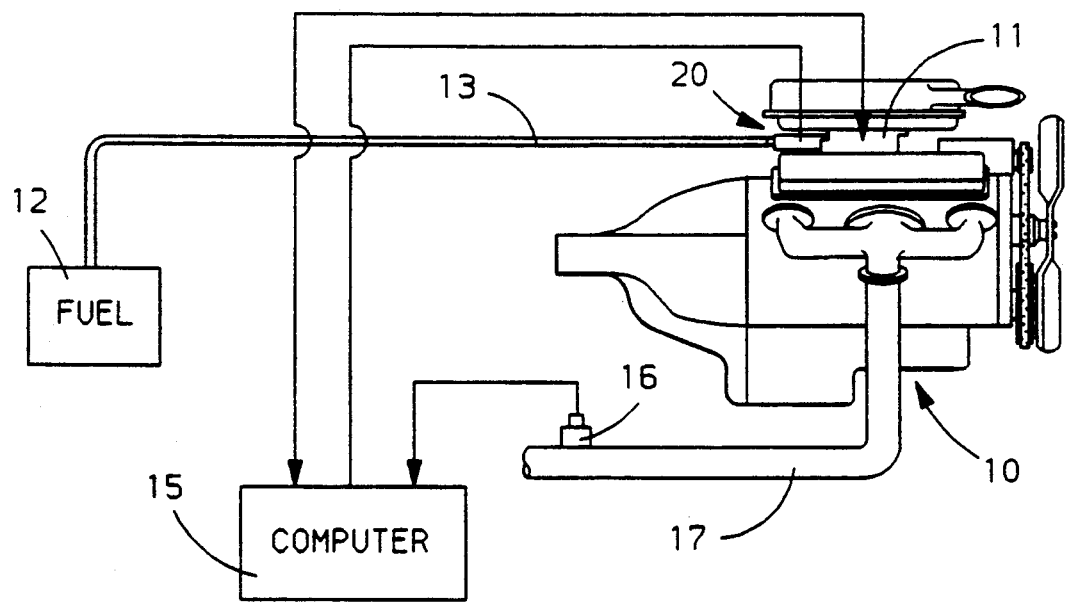
FIG. 1 illustrates an internal combustion engine adapted to operate on a variable alcohol-gasoline fuel mixture along with the engine computer control system.

Referring to FIG. 1, there is shown an internal combustion engine 10 conventionally adapted to operate on a variable alcohol-gasoline fuel mixture, along with a control system for adjusting engine fueling based upon the sensed relative proportion of a known alcohol in the fuel mixture. As illustrated, engine 10 is equipped with a fuel supply system, which includes a fuel tank 12, a fuel supply line 13, a fuel composition sensor 20, and a fuel injection system 11 for delivering fuel for combustion. The fuel system also includes other standard components such as a fuel pump and fuel filter that have not been specifically shown in FIG. 1.

During the conventional operation of engine 10, a fuel mixture containing a known alcohol and gasoline, in an unknown ratio, is pumped from fuel tank 12 through the fuel supply line 13 to the fuel composition sensor 20, and then to the fuel injection system 11. The quantity of fuel delivered to engine 10 by the fuel injection system 11 is controlled in response to a fuel control signal applied by computer 15. Computer 15 is a programmed digital computer of the type generally used for engine control and is well known in the prior art in many variations. Typically, computer 15 includes a central processing unit, random access memory, read only memory, analog-to-digital and digital-to-analog converters, input/output circuitry, and clock circuitry.

Normally, computer 15 receives input signals from a variety of engine and environmental parameter sensors, such as exhaust gas oxygen sensor 16 in exhaust line 17, in order to generate the appropriate fuel control signal for the engine fuel injection system 11. The fuel control signal typically takes the form of a timed fuel pulses applied to individual fuel injectors, where the width of each fuel pulse (FPW) determines the length of time that each fuel injector is open, and hence the quantity of fuel delivered to the engine.

As is well known, the quantity of fuel delivered to engine 10 (as determined by the fuel pulse width FPW) must be adjusted based upon the relative concentrations of alcohol and gasoline in the fuel mixture to achieve clean, efficient combustion and acceptable engine performance, see for example U.S. Pat. No. 4,955,345 issued to Brown et al. on Sep. 11, 1990, which is assigned to the same assignee as the present application and is hereby incorporated by reference.

To this end, fuel composition sensor 20 measures the relative proportion of an alcohol to gasoline in the fuel mixture delivered to engine 10, and generates a fuel composition signal for use by computer 15. Any one of several fuel composition sensors known in the art may be employed; however, for the purpose of describing the present invention, sensor 20 will be considered to be a capacitive type sensor for measuring the dielectric constant of the fuel flowing to engine 10. A detailed description of the physical structure for such a capacitive sensor 20 and its associated measuring circuitry is provided in U.S. Pat. No. 4,915,084 issued to E. V. Gonze on Apr. 10, 1990, which is assigned to the same assignee of the present application and is hereby incorporated by reference into the present application.

As is well known, the dielectric constant of an alcohol-gasoline fuel mixture can be directly related to the proportion of alcohol in the mixture. The mechanical structure of the preferred capacitive sensor 20 is such that fuel flowing through it passes between, and in contact with, two separated electrodes that are coupled to a capacitance measuring circuit. Sensor 20 determines the dielectric constant of the fuel mixture passing through it, and generates an output capacitance signal, which is directed to computer 15. Also, as described in the above referenced U.S. Pat. No. 4,915,084, fuel composition sensor 20 can provide computer 15 with an input signal indicative of the temperature of the fuel mixture entering engine 10 to compensate for minor variations in measured fuel capacitance with temperature. The relative proportion of alcohol in the fuel mixture is then normally derived from a look-up table based upon the values of the measured fuel capacitance and fuel temperature.

To achieve optimal combustion, it is also known that a warmed-up engine running on a variable alcohol-gasoline fuel must be operated at stoichiometric air/fuel ratio, which depends upon the relative proportion of alcohol to gasoline in the fuel mixture. This can be accomplished, for example, by sensing the capacitance of the fuel mixture, determining the stoichiometric air/fuel ratio as a table look-up based upon the sensed fuel capacitance, and then adjusting the duration of injector fuel pulse signals, i.e. FPW, in conventional closed-loop fashion to achieve optimal combustion at the determined stoichiometric air/fuel ratio (see the above referenced U.S. Pat. No. 4,915,084).

For a given type of alcohol, such as ethanol or methanol, the above described capacitive sensor 20 can be calibrated to accurately determine the relative proportion of that particular alcohol to gasoline in the mixture, but it is not capable of distinguishing which type of alcohol is blended with the gasoline. Once an engine has warmed-up, the particular type of alcohol in the fuel blend is of little consequence since the closed-loop engine fuel control system then becomes operative and can maintain the air/fuel ratio at the optimum stoichiometric value, no matter what type of alcohol is present in the fuel mixture.

Due to the low volatility of ethanol and methanol, the fraction of gasoline in an alcohol-gasoline mixture provides most of the combustible vapor when the engine is started, and first operated at low ambient temperatures. Consequently, engines operated on fuel mixtures having high alcohol concentrations are usually difficult to start at low temperatures, and vehicles employing such engines typically exhibit poor driveability during the engine warm-up period. The conventional approach to solving these problems has been to appropriately increase the amount of the fuel delivered to an engine during these operating periods, in accordance with the relative proportion of the particular alcohol to gasoline in the fuel mixture, thereby assuring that a sufficient amount of gasoline vapor is present for combustion (see for example the above referenced U.S. Pat. No. 4,955,345).

The problem with this prior art approach is that the type of alcohol in the blended fuel mixture must be known apriori to regulate the fuel properly during cold starting and engine warm-up, since the engine control computer is customarily calibrated or programmed for engine operation with a variable ethanol-gasoline fuel mixture or a variable methanol-gasoline fuel mixture, but not for both types of alcohol blends. Once the engine control system is calibrated for a particular type of alcohol-gasoline fuel mixture, engine cold starting and warm-up performance can be significantly degraded if the engine is then operated with a fuel blend containing a different type of alcohol. This occurs because alcohols such as ethanol and methanol each have different properties, and a fuel composition sensor calibrated for use with one type of alcohol blend will not indicate the correct fraction of gasoline in the fuel mixture when another type of alcohol blend is used to operate the engine As a result, the fuel mixture delivered to the engine during cold starting and warm-up (when closed-loop fuel control is inoperative) will be either too rich or too lean, and the engine may not start or run smoothly.

Consequently, there exists a need for an apparatus for discriminating between different types of alcohols such as ethanol and methanol in alcohol-gasoline fuel mixtures delivered to an engine and a system for controlling fueling based upon the determined type of alcohol in the fuel mixture.

Figure 2:
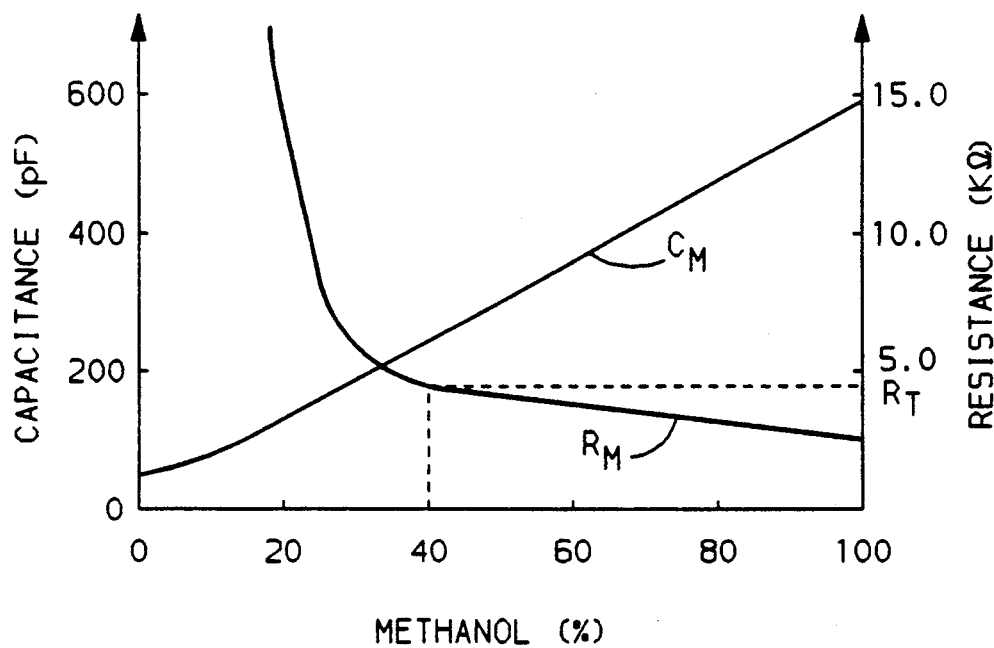
FIG. 2 graphically illustrates the variation in the measured capacitance and resistance of methanol-gasoline fuel mixtures as a function of methanol concentration.
Figure 3:
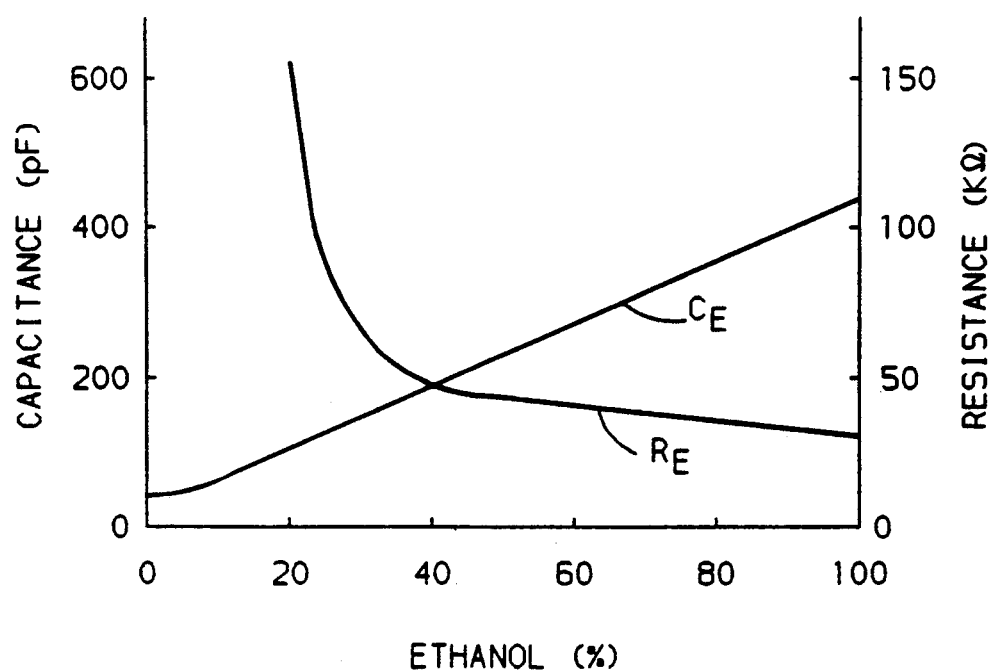
FIG. 3 graphically illustrates the variation in the measured capacitance and resistance of ethanol-gasoline fuel mixture as a function of ethanol concentration.

Referring now to FIG. 2 and 3, there are shown graphical representations of the electrical capacitance and resistance of variable methanol-gasoline mixtures and variable ethanol-gasoline mixtures measured across the sensing electrodes of the prior art sensor 20 described in the above U.S. Pat. No. 4,915,084. The resistance and capacitance data was measured by connecting a standard commercially available impedance meter across the sensor electrodes and then varying the composition of the fuel mixture flowing through the sensor.

The curves $C_M$ and $C_E$ in FIGS. 2 and 3 represent the capacitance of variable methanol-gasoline and variable ethanol-gasoline mixtures, respectively, at a fixed fuel temperature of approximately 24° C. As illustrated, these curves increase in an approximately linear fashion as the percentage of alcohol to gasoline in the mixture increases. This is due to the differences between the dielectric constants of alcohols and gasoline. Methanol has a relative dielectric constant in the order of 33.6, as compared with 25.7 for that of ethanol, and 2.1 for that of gasoline. As will be understood by those skilled in the art, the effective dielectric constant of a particular fuel mixture is equal to the measured capacitance multiplied by a constant, where the value of the constant is determined by the physical geometry of the sensing electrodes (i.e. size, spacing, and, shape). Thus, for a particular sensor geometry, the measured capacitance of the fuel mixture is indicative of, and can be directly related to, the dielectric constant of the fuel mixture. As illustrated, the measured capacitance (or dielectric constant) of methanol-gasoline mixtures will be greater than that of ethanol-gasoline mixtures having the same percentage of alcohol, since methanol has a larger dielectric constant than ethanol.

The curves $R_M$ and $R_E$ in FIGS. 2 and 3 represent, respectively, the measured resistance appearing across the sensing electrodes of sensor 20 for variable methanol-gasoline mixtures and variable ethanol-gasoline mixtures. As will be understood, the fuel resistivity is equivalent to the measured sensor resistance multiplied by a constant, which is also determined by the geometry of the sensing electrodes. Thus, for a particular sensor geometry, the measured resistance of the fuel mixture is indicative of, and can be directly related to, the resistivity of the fuel mixture. Although not shown in FIGS. 2 and 3, measurements have indicated that the resistivity of alcohol-gasoline fuel mixtures increase slightly with decreasing fuel temperature.

When the relative proportion of alcohol (either ethanol or methanol) in the fuel mixtures depicted in FIGS. 2 and 3 exceeds approximately 40% (by volume), the fuel resistivity remains relatively constant for further increases in methanol or ethanol concentration. Additionally, it has been found that the resistivity of relatively pure ethanol-gasoline mixtures are generally at least an order of magnitude greater than that of methanol-gasoline mixtures having the same relative proportion of alcohol to gasoline.

As discussed in a related and copending U.S. Pat. Application Ser. No. 07/752344, which is assigned to the same assignee of the present application, alcohol-based fuel mixtures have the capacity to dissolve significant quantities of water and other ionic contaminants. These dissolved contaminants have the effect of decreasing the resistivity of alcohol-gasoline fuel mixtures. However, the amount of contaminants in commercially available alcohol-gasoline fuel mixtures is never expected to reach a level where the resistivity of ethanol-gasoline mixtures will fall below that of methanol-gasoline mixtures. As a consequence, it has been recognized that the fuel mixture resistivity can be utilized to determine whether an alcohol-gasoline fuel mixture contains ethanol or methanol.

Figure 4:
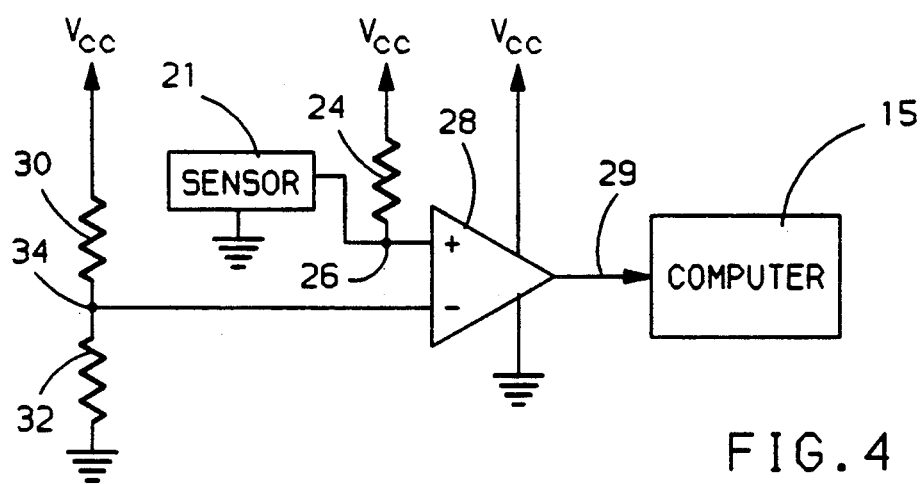
FIG. 4 illustrates an apparatus for determining and indicating the type of alcohol contained in an alcohol-gasoline fuel mixture based on measured fuel mixture resistivity.

Referring now to FIG. 4, there is shown a simple embodiment for determining the type of alcohol contained in an alcohol-gasoline fuel mixture based on its measured resistivity. Consider for the present that a fuel resistivity sensor 21 has the same physical structure as the fuel composition sensor described in the above mentioned U.S. Pat. No. 4,915,084, and that it is inserted in the fuel supply line 13 of engine 10 in the same manner as the fuel composition sensor 20 depicted in FIG. 1. This being the case, the resistance appearing between the sensing electrodes of sensor 21 will vary as illustrated by curve $R_M$ in FIG. 2 for methanol-gasoline fuel mixtures, and as illustrated by curve $R_E$ in FIG. 3 for ethanol-gasoline fuel mixtures.

A circuit for measuring the resistance of fuel sensor 21, and hence the resistivity of the fuel mixture, is formed by connecting a resistor 24 to sensor 21 at junction 26, and then connecting this series combination of the resistor 24 and sensor 21 between electrical ground and a fixed voltage potential $V_{cc}$, such as provided by a conventional regulated power supply (not shown). It will be understood by those skilled in the art that this fashion of connecting sensor 21 and resistor 24 forms a voltage divider, and the magnitude of the voltage potential appearing at junction 26 represents a resistance signal indicative of the resistance of sensor 21, and hence the resistivity of the alcohol-fuel mixture flowing through it.

The value of resistor 24 is set at approximately the midpoint of the desired range of resistance to be measured by sensor 21. This tends to equalize the sensitivity of the resistance signal appearing at junction 26 for similar changes in sensor resistance over the desired range of resistance. For example, when sensor 21 has the physical structure described in U.S. Pat. No. 4,915,084, the sensor resistance will vary in the range from 0-10 KΩ for methanol-gasoline fuel mixtures containing at least 20% methanol. For this range of sensor resistance, the value of resistor 24 might, for example, be set at 5 KΩ.

In order to provide computer 15 with a signal indicating the type of alcohol in the fuel, the resistance signal at junction 26 is coupled to the non-inverting input of a conventional operational amplifier 28, which is configured to operate as a comparator. For this type of operation, resistors 30 and 32 are connected in series to form a junction 34 between electrical ground and the voltage potential $V_{cc}$. Junction 34 is then connected to the inverting input of the operational amplifier 28. In this configuration, the operational amplifier 28 functions as a voltage comparator, i.e. the voltage of the resistance signal at the non-inverting input is compared with the voltage appearing at the inverting input. When the voltage of the resistance signal is greater than the voltage at the inverting input, the output 29 of operational amplifier 28 is held at approximately the voltage potential $V_{cc}$. On the other hand, if the voltage of the resistance signal falls below the voltage at the negative input, the output 29 of the operational amplifier 28 switches to ground potential.

The threshold at which the output voltage of operational amplifier 28 switches to a high state (Vcc) is determined by the values of resistors 30 and 32. when resistors 30 is selected to have the same value as resistor 24 (i.e , 5 kΩ in the present embodiment), the value of resistor 32 then corresponds to a fixed threshold resistance value for the fuel resistance measured by sensor 21, below which the output of the operational amplifier 28 will switch to a low state (ground potential). Consequently, if resistor 32 is selected to have a threshold resistance value of say $R_T$ as shown in FIG. 2, the output voltage of operational amplifier 28 will be at its high state when the resistance of sensor 21 is greater than $R_T$, and at its low state when the resistance of sensor 21 is less than or equal to $R_T$.

In practice the actual value of resistor 32 (threshold resistance value) can be set equal to (or perhaps just slightly greater than) the largest expected sensor resistance for say a 40% methanol-gasoline fuel mixture over the entire range of fuel temperatures encountered during normal engine operation. This being the case, the voltage level at the output 29 of operational amplifier 28 then provides an accurate indication of the type of alcohol (either ethanol or methanol) in fuel mixtures, provided the mixtures contain at least 40% alcohol. The output voltage of operational amplifier 28 will be at its high state for ethanol, and at its low state for methanol. Note that this embodiment then provides computer 15 with an indication of the type alcohol in the fuel mixture, which could be used for example to set an internal flag in memory to indicate the type of alcohol.

It will be recognized that in selecting the value of resistor 32 in the above fashion, the threshold resistance value will be fixed at a constant value, and methanol-gasoline fuel mixtures containing less than 40% methanol will be incorrectly indicated as containing ethanol. With regard to engine fuel control during cold starting and warm-up, this has been found quite acceptable since the actual fraction of gasoline in a methanol-gasoline fuel mixture incorrectly indicated as containing ethanol does not differ significantly from the fraction of gasoline that would be contained in the incorrectly indicated ethanol-gasoline mixture when the alcohol concentration is in the order of 40% or less. As a result, engine cold starting and warm-up operation are not significantly degraded if a fuel mixture containing less than 40% methanol is incorrectly indicated as being an ethanol-gasoline fuel mixture.

Figure 5:
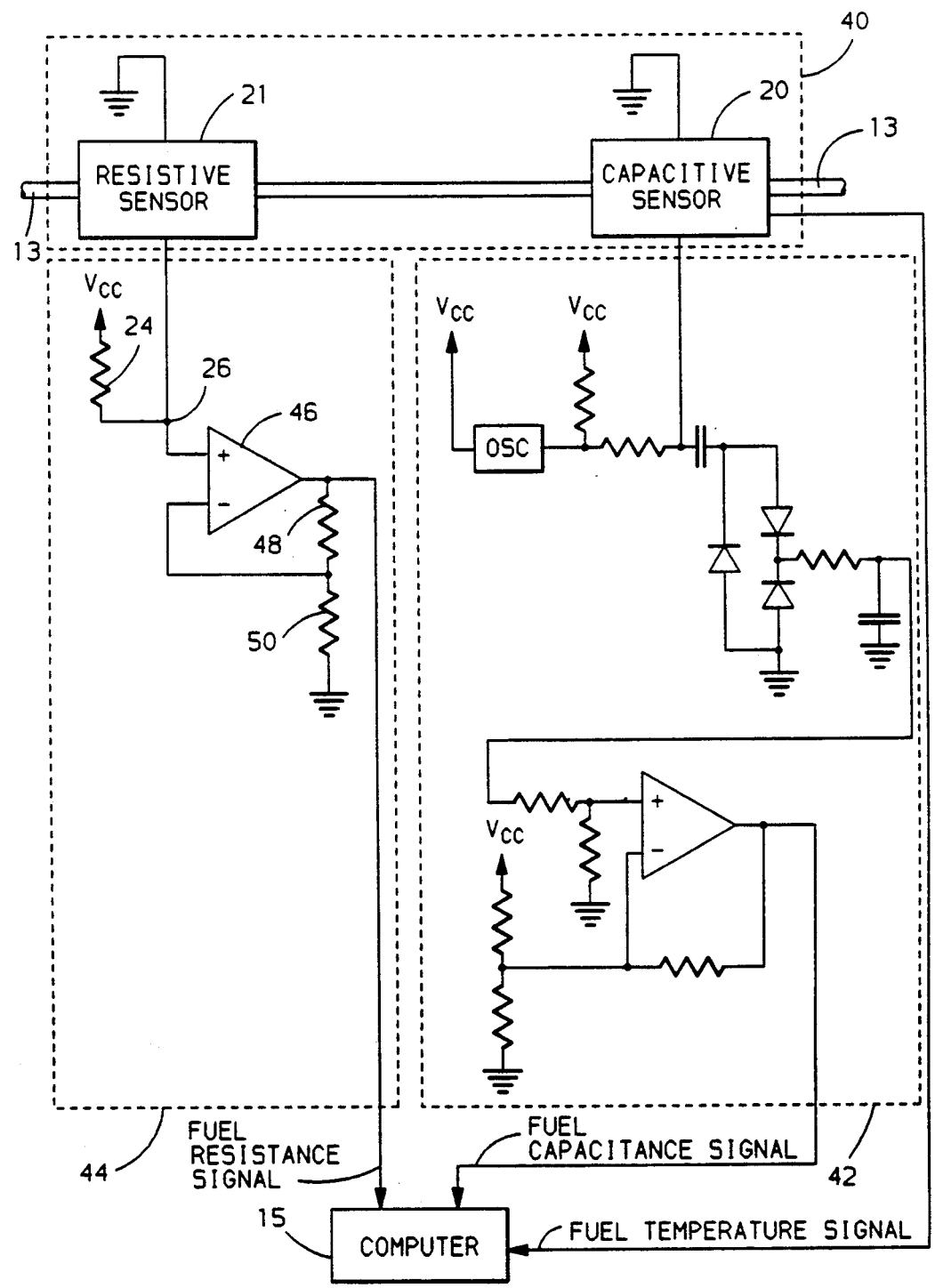
FIG. 5 illustrates an apparatus for determining and indicating the type of alcohol contained in an alcohol-gasoline fuel mixture based on the measured fuel mixture resistivity and dielectric constant.

Referring now to FIG. 5, there is shown another embodiment for determining the type of alcohol in the fuel mixture, which further includes means for measuring the dielectric constant (capacitance) and temperature of the fuel mixture. As will be described, this embodiment provides for establishing a resistive threshold amount based upon the measured dielectric constant and/or temperature of the fuel mixture. By selecting the resistive threshold in this fashion, a type of alcohol in the fuel mixture can be determined more accurately and over a wider range of alcohol concentrations.

In this embodiment, a sensor means generally designated as 40 is positioned in the engine fuel supply line 13. This sensor means 40 includes the previously mentioned prior art capacitive sensor 20 for measuring fuel temperature and dielectric constant, and a resistive sensor 21 for measuring the resistivity of the fuel mixture.

Capacitive sensor 20 is coupled to a capacitance measuring circuit 42, which develops an output fuel capacitance signal directed to computer 15. This output capacitance signal is indicative of the dielectric constant of the fuel mixture flowing through sensor 20. Capacitive sensor 20 and capacitance measuring circuit 42 are identical in structure and function to that described in the above incorporated U.S. Pat. No. 4,915,084, and will not be discussed further in the present application. Likewise for the the fuel temperature sensor contained within the structure of sensor 20 that provides computer 15 with a fuel temperature signal.

At this point in the discussion, resistive sensor 21 will be considered to have the same physical structure as that of the prior art capacitive fuel sensor 20, although, any known sensor configuration capable of measuring fuel resistivity could be used as an alternative. Resistive sensor 21 is coupled to a resistance measuring circuit 44, which includes a resistor 24 connected in series with sensor 21 across electrical ground and the fixed voltage potential $V_{cc}$, thereby forming a voltage divider as discussed in the description associated with FIG. 4. Again, the magnitude of the voltage that appears at junction 26, represents a resistance signal indicative of the sensor resistance, and hence fuel resistivity. In this embodiment, the resistance signal is directed to the non-inverting input of an operational amplifier 46 that is configured for amplifier operation. The output signal provided by the operational amplifier 46 represents an amplified version of the fuel resistance signal, which is then provided as an input to computer 15. As will be recognized by those skilled in the art, the gain of the amplifier is fixed by the values of resistors 48 and 50, which are generally selected to maximize the voltage swing of the amplifier output signal, while ensuring compatibility with the input analog-to-digital conversion circuitry of computer 15.

Figure 6:
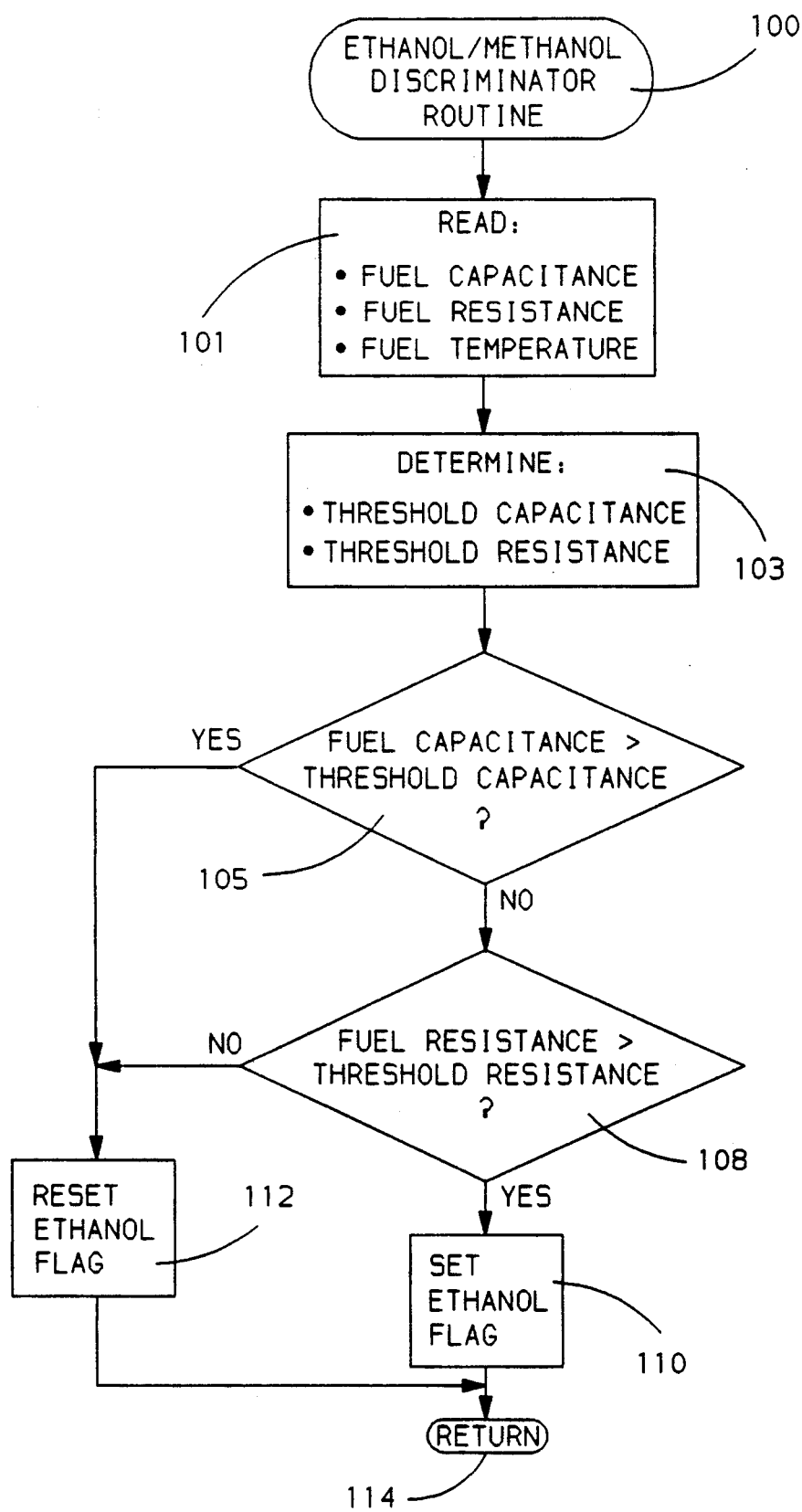
FIG. 6 shows a flow diagram representative of the steps executed by the computer shown in FIG. 5, when determining and indicating the type of alcohol contained in an alcohol-gasoline fuel mixture based on the measured fuel mixture resistivity and dielectric constant.

Referring now to FIG. 6, there is shown a flow diagram representative of the steps in an ETHANOL/-METHANOL DISCRIMINATOR ROUTINE, which is executed by computer 15 as part of the main engine control program in carrying out the present invention. The routine is entered at point 100 and immediately proceeds to step 101.

At step 101, the values of the fuel resistance, fuel capacitance, and fuel temperature signals input into computer 15 are read and stored in memory for subsequent use.

Next at step 103, a threshold capacitance value and a threshold resistance value are derived by computer 15. These values could be stored fixed constants, in which case, the threshold capacitance value can be set equal to (or just slightly greater than) the largest expected capacitance measured by sensor 20 for a 100% ethanol fuel mixture (over the range of normally encountered fuel temperature), and the threshold resistance value can be fixed as described in the previous embodiment. However, for improved accuracy, the threshold capacitance and resistance values can be obtained from stored look-up tables. For example, a look-up table for threshold capacitance could contain measured capacitance values for 100% ethanol fuel as a function of the fuel temperature read at step 101. The look-up table for threshold resistance could contain data representing the measured resistance for methanol-gasoline fuel mixtures (such as provided by curve $R_M$ in FIG. 2) as a function of the measured fuel capacitance and temperature found at step 101. Alternatively, threshold resistance values could be stored in the look-up table as a function of only measured fuel capacitance, if the threshold values are selected to be the maximum measured fuel resistance expected to be encountered over the normal range of fuel temperature. In which case, the fuel temperature would not have to be read at step 101.

After completing step 103, the routine passes to step 105, where a decision is required as to whether the value of the fuel capacitance signal read at step 101 is greater than the threshold capacitance value derived at step 103. If the value of the fuel capacitance is greater than the threshold capacitance value, the fuel is judged to contain methanol, since the threshold capacitance represents the maximum possible capacitance that a mixture containing ethanol can have. The routine then proceeds to step 112. If the fuel capacitance does not exceed the threshold capacitance value, the fuel can contain either methanol or ethanol, and the routine then proceeds to step 108.

At step 108, a decision is required as to whether the value of the fuel resistance read at step 101 is greater than the threshold resistance value derived at 103. If the fuel resistance exceeds this threshold resistance value, the fuel is judged to contain ethanol, since the threshold resistance value represents the maximum resistance expected to be measured for a fuel mixture containing methanol. The routine then proceed to step 110. If the fuel resistance does not exceed the threshold resistance value, the fuel mixture is judged to contain methanol and the routine proceeds to step 112.

When the routine passes from decision step 108 to step 110, an ethanol flag is set in memory to indicate that the alcohol in the fuel mixture is ethanol.

When the routine passes to step 112 from either of the decision steps at 105 or 108, the ethanol flag is reset to indicate that the fuel mixture has been judged to contain methanol rather than ethanol.

After the ethanol flag is set or reset at steps 110 or 112 to indicate the type of alcohol contained in the fuel mixture, the program proceeds to point 114 to exit the routine.

It should be noted that in the above routine, step 105 can be completely removed, without influencing the accuracy of the decision as to whether the fuel mixture contains methanol or ethanol. Step 105 merely provides a convenient way to bypass the decision required at step 108, in those instances when the fuel mixture contains such a large concentration of methanol that the measured capacitance exceed the maximum possible capacitance for a 100% ethanol fuel.

Figure 7:
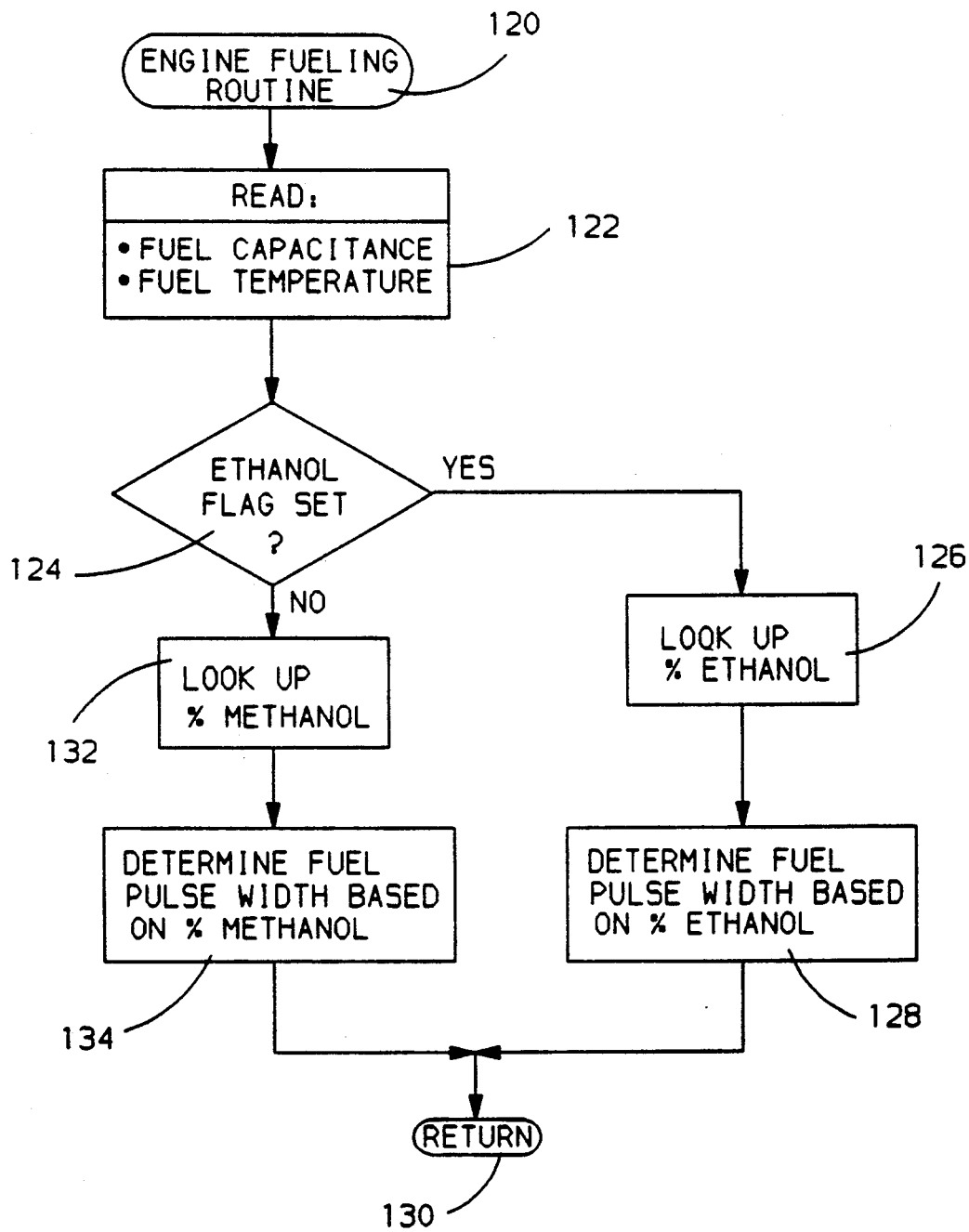
FIG. 7 show B a flow diagram representative of the steps executed by the computer shown in FIG. 5, when controlling the quantity of the alcohol-gasoline fuel mixture delivered to the engine in accordance with the type and concentration of alcohol determined to be present in the alcohol-gasoline fuel mixture.

Referring now to FIG. 7, there is shown an ENGINE FUELING ROUTINE routine that can be executed by computer 15 for controlling the quantity of alcohol-gasoline fuel delivered to engine 10 based upon the type of alcohol determined to be present in the fuel mixture, as indicated, for example, by any of the above described embodiments. The ENGINE FUELING ROUTINE is executed as part of the main loop engine control program continuously executed by computer 15 in controlling the operation of engine 10.

The routine is entered at point 120 and proceeds to step 122 where the measured values for the fuel capacitance and fuel temperature are read by the program.

Next at step 124, a decision is required as to whether the ethanol flag has been set or reset (see steps 110 and 112 in the routine of FIG. 6. If the ethanol flag has been set, indicating that the alcohol in the fuel mixture is ethanol, the routine passes to step 126. If the ethanol flag has been reset, indicating that the alcohol in the fuel mixture is methanol, the routine proceeds to step 132.

When the routine proceeds to step 126 from step 124, the concentration (or percentage) of ethanol in the fuel mixture is determined by a table look-up as a function of the measured fuel capacitance and temperature read at step 122. Table values for the percent ethanol as a function of capacitance can be obtained from data, such as illustrated by curve $C_E$ in FIG. 3, measured at a number of different fuel temperatures.

Next at step 128, a value for the fuel injection pulse width FPW is determined based upon the percent ethanol in the fuel mixture found at step 126. Customarily, the duration of the fuel injection pulse width is increased during engine cranking and the initial warm-up period depending upon the type and percentage of alcohol in the fuel mixture. For example, a cranking fuel pulse width can be obtained as a table look-up as a function of alcohol concentration (percentage) and engine coolant temperature, as described in U.S. Pat. No. 4,955,345, which has previously been incorporated by reference. As described therein, during the warm-up period after the engine has started, the cranking fuel pulse width value is blended to equal the normal fuel pulse width value provided by the conventional closed-loop fuel control algorithm. Alternatively, several other techniques and/or algorithms exist in the prior art for computing fuel pulse width, once the type and ratio of alcohol to gasoline in the fuel mixture is known, and any of these could be employed for controlling the quantity of the fuel mixture delivered to the engine. Once the appropriate fuel pulse width is determined in accordance with the proportion of ethanol in the fuel mixture, the FPW value is stored in memory at step 128 for later use in the main engine control program when computer 15 controls the fuel injection system 11 so that the appropriate quantity of fuel mixture is delivered to engine 10.

When the routine proceeds to step 132 from step 124, the concentration (percentage) of methanol in the fuel mixture is determined by a table look-up, as a function of the measured fuel capacitance and temperature found at step 122. Table values for the percent methanol as a function of capacitance can be obtained from data, such as illustrated by curve $C_M$ in FIG. 2, measured at a number of different fuel temperatures.

Next at step 134, a value for the fuel injection pulse width FPW is determined based upon the methanol concentration in the fuel mixture found at step 132. Again, as in step 128, the conventional practice is to increase the fuel injection pulse width during engine cranking and the initial warm-up period depending upon the percentage of methanol in the fuel mixture. The fuel pulse width determined at this step is then stored for later use by computer 15 when controlling the quantity of fuel mixture delivered to the engine by injection system 11.

After completing either step 128 or step 134, the routine exits to the main engine control program via point 100.

In the above described embodiments of the present invention, the resistive fuel sensor 21 was described as having the same physical structure of the prior art capacitive sensor disclosed in U.S. Pat. No. 4,915,084. This was done primarily to facilitate and simplify the description, and should be considered as merely exemplary and not limiting with respect to the present invention. The fuel sensor 21 may in fact have any possible physical configurations that is capable of providing an indication of fuel mixture resistivity.

Figure 8:
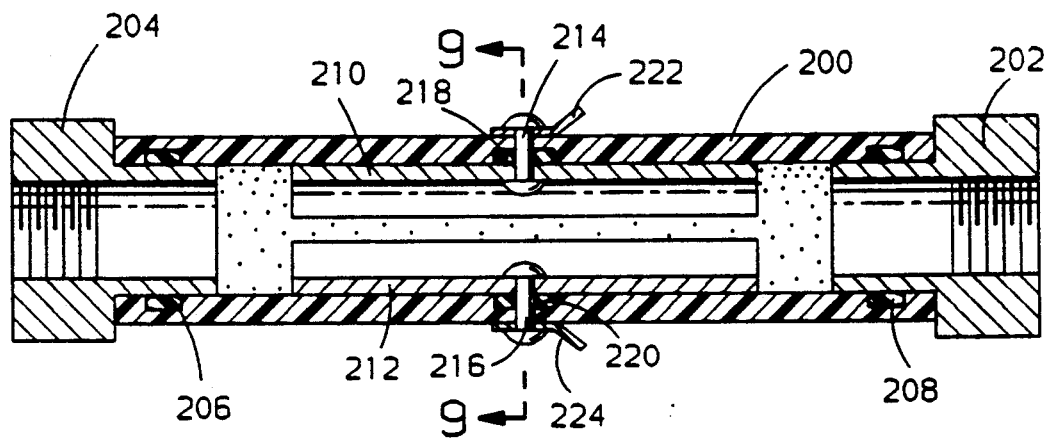
FIG. 8 shows a cutaway view of an alternative sensor for measuring the resistivity of an alcohol-gasoline fuel mixture.
Figure 9:
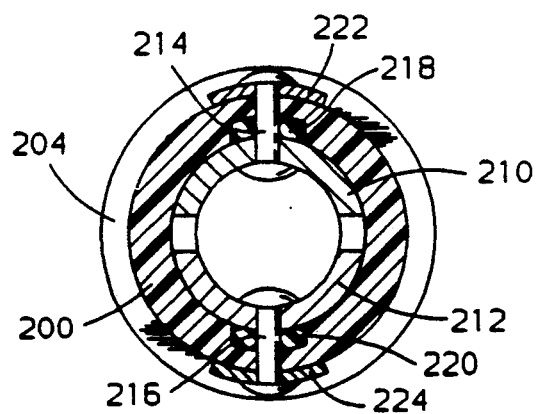
FIG. 9 shows a sectional view of the fuel sensor shown in FIG. 8 along the line 9—9.

Referring now to FIGS. 8 and 9, there are shown respectively, a cutaway view of an alternative resistive fuel sensor and a sectional view of the sensor along the line 9—9 of FIG. 8. A cylindrical casing 200 is formed of an electrically non-conducting material such as nylon, which is resistant to alcohol-gasoline fuel mixtures. Stainless steel fuel line fittings 202 and 204 are inserted into the open ends of casing 200. O-rings 206 and 208 are employed to preventing the leakage of fuel between the casing 200 and the inserted fuel line fittings 202 and 204. Two stainless steel electrodes 210 and 212 are spaced apart inside the cylindrical casing 200, and are held in position by electrically conducting rivets 214 and 216, which respectively pass through electrodes 210 and 212 and the walls of casing 200 as illustrated. Terminals 222 and 224 are fixed between the casing 200 and the flattened ends of rivets 214 and 216 to provide a means for making electrical connection to the internal sensing electrodes 210 and 212. O-rings 218 and 220 surrounding rivets 214 and 216 prevent fuel from leaking between the casing and rivets.

The resistance appearing across the terminals 222 and 224 of the alternative sensor configuration will be representative of the resistivity of the fuel mixture flowing through casing 200. Since the physical structure of the alternative fuel sensor differs from that of prior art sensor 20 described in U.S. Pat. No. 4,915,084, it will be understood that different resistors and different threshold resistance values will generally be required when using this or other alternative sensors in the previously described embodiments.

Also, as described in previously referenced U.S. Pat. Application Ser. No, 07/752,344, a single fuel sensor can be switched under the control of computer 15 to measure the both the resistance and capacitance of a fuel mixture, if so desired.

The above embodiments have been described with regard to alcohol-gasoline fuel mixtures containing either ethanol or methanol, since these two types of alcohol-gasoline fuels appear to be the most commercially viable at the present time. It will be recognized that the invention can also be used to discriminate between other types of alcohol-gasoline fuel mixtures having sufficiently different electrical resistivities. Consequently, the present invention should not be contemplated as being limited to alcohol-gasoline fuel mixtures containing only ethanol or methanol.

Thus, the aforementioned description of the preferred embodiments of the invention is for the purpose of illustrating the invention, and is not to be considered as limiting or restricting the invention, since many modifications may be made by the exercise of skill in the art without departing from the scope of the invention.

The embodiments of the invention in which an exclusive property or privilege is claimed are defined as follows:

1. A discriminator apparatus for identifying the type of alcohol contained in an alcohol-gasoline fuel mixture delivered to an internal combustion engine, the discriminator apparatus comprising:
   a sensor for measuring the electrical resistivity of the fuel mixture and for developing a signal indicative of the fuel mixture resistivity;

means responsive to the signal developed by the sensor for determining the type of alcohol contained in the fuel mixture;

means for providing an output signal indicative of the type of alcohol determined to be present in the fuel mixture.

2. A discriminator apparatus for identifying the type of alcohol contained in an alcohol-gasoline fuel mixture delivered to an internal combustion engine, where the alcohol is from the group consisting of ethanol and methanol, the discriminator apparatus comprising;

a resistive sensor for measuring the electrical resistivity of the fuel mixture and for developing a resistance signal having a value indicative of the fuel mixture resistivity;

means for deriving a threshold resistance value;

means for comparing the value of the resistance signal with the threshold resistance value;

means for providing an output signal indicating that ethanol is contained in the fuel mixture when value of the resistance signal is greater than the threshold resistance value and indicating that methanol is contained in the fuel mixture when the value of the resistance signal is less than the threshold resistance value.

3. The discriminator apparatus as described in claim 2, wherein the threshold resistive value is a predetermined constant value.

4. The discriminator apparatus as described in claim 2, which further includes a capacitance sensor for measuring the dielectric constant of the fuel mixture and for developing a capacitance signal having a value indicative of the fuel mixture dielectric constant, wherein the threshold resistive value is derived based upon the value of the capacitance signal.

5. The discriminator apparatus as described in claim 4, which further includes means for indicating that the fuel mixture contains ethanol when the value of the capacitance signal exceed a predetermined threshold capacitance value.

6. The discriminator apparatus as described in claim 2, which further includes:

a capacitance sensor for measuring the dielectric constant of the fuel mixture and for developing a capacitance signal having a value indicative of the fuel mixture dielectric constant;

a temperature sensor for measuring the temperature of the fuel mixture and for developing a temperature signal having a value indicative of the temperature of the fuel mixture delivered to the engine, wherein the threshold resistance value is derived based upon the values of the capacitance signal and the temperature signal.

7. The discriminator apparatus as described in claim 6, which further includes means for indicating that fuel mixture contains ethanol when the value of the capacitance signal exceed a predetermined threshold capacitance value.

8. A fuel control system for an internal combustion engine operated on an alcohol-gasoline fuel mixture, the control system comprising:

sensor means for identifying the type and relative concentration of alcohol contained in the alcohol-gasoline fuel mixture;

means for controlling the quantity of fuel delivered to the engine based upon the identified type and relative concentration of alcohol in the fuel mixture.

9. A fuel control system for an internal combustion engine operated on an alcohol-gasoline fuel mixture, the control system comprising:

a sensor for identifying the type of alcohol contained in the alcohol-gasoline fuel mixture;

means for determining the relative concentration of alcohol to gasoline in the fuel mixture in accordance with identified type of alcohol in the fuel mixture; and means for controlling the quantity of fuel delivered to the engine based upon the identified type and concentration of alcohol in the fuel mixture.

10. The fuel control system described in claim 9, wherein the type of alcohol contained in the fuel mixture is one from a group consisting of ethanol and methanol.

11. A fuel control system for an internal combustion engine operated on an alcohol-gasoline fuel mixture, the fuel control system comprising:

a resistive sensor for measuring the resistivity of the fuel mixture and for developing a resistance signal indicative of fuel mixture resistivity;

a capacitive sensor for measuring the dielectric constant of the fuel mixture and for developing a capacitance signal indicative of the fuel mixture dielectric constant;

means responsive to the resistance and capacitance signals for determining the type and concentration of alcohol in the fuel mixture;

means for controlling the quantity of fuel mixture delivered to the engine in accordance with the determined type and concentration of alcohol in the fuel mixture.

12. The fuel control system described in claim 11, wherein the type of alcohol contained in the fuel mixture is one from a group consisting of ethanol and methanol.

13. The fuel control system described in claim 11, wherein the relative concentration of the alcohol to gasoline in the fuel mixture is determined in accordance with the dielectric constant of the fuel mixture and the type of alcohol determined to be present in the fuel mixture.

* * * * *